April 11, 1961 W. E. LAMMERTS Plant Pat. 2,045
ROSE PLANT
Filed July 6, 1960
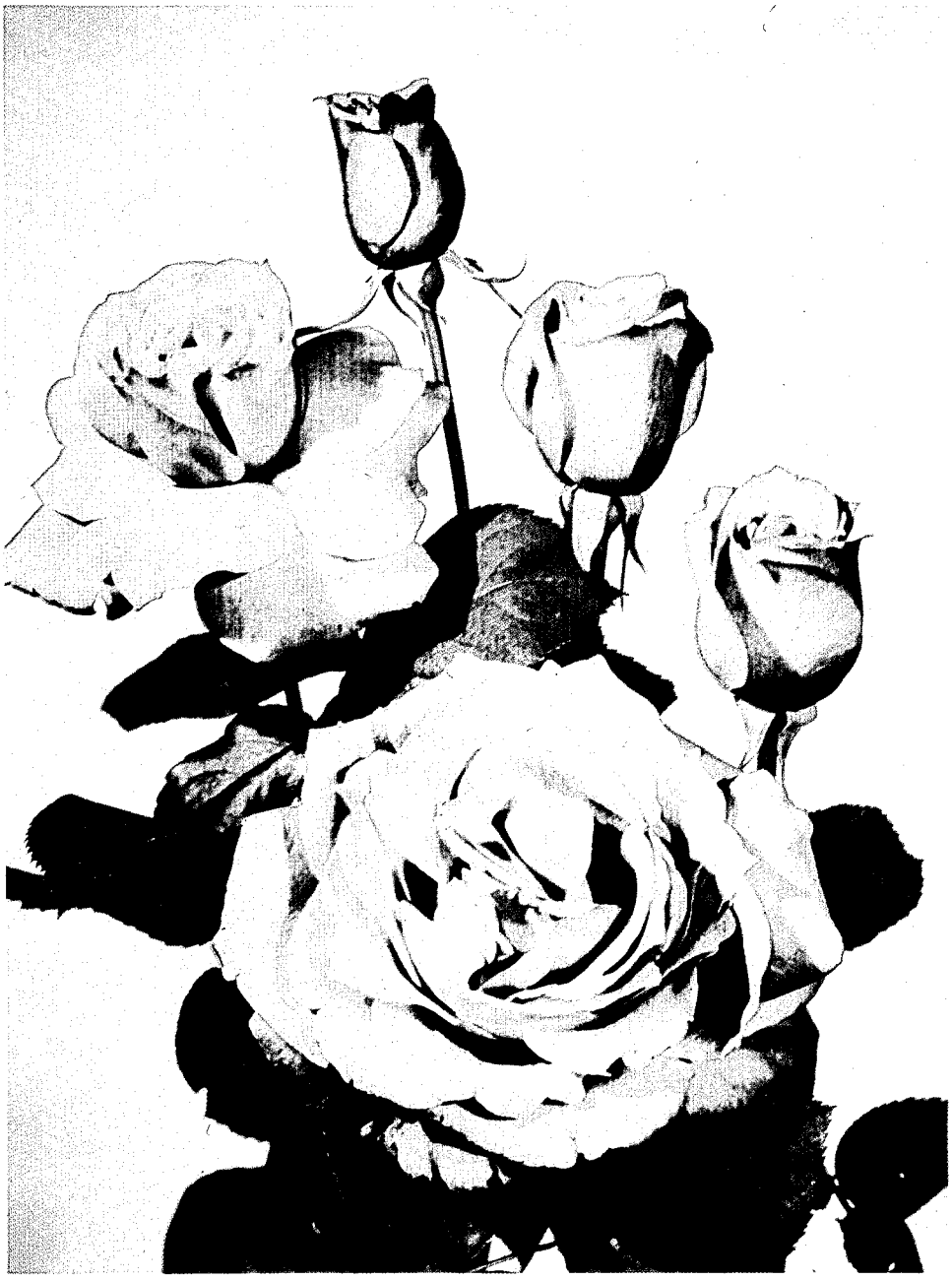
INVENTOR:
WALTER E. LAMMERTS
BY Rummler & Snow
ATT'YS United States Patent Office Plant Pat. 2,045
Patented Apr. 11, 1961

2,045

ROSE PLANT

Walter E. Lammerts, Livermore, Calif., assignor to Amling-Devor Nurseries, Inc., Livermore, Calif., a corporation of California Filed July 6, 1960, Ser. No. 41,220

1 Claim. (Cl. 47—61)

My present invention relates to rose plants and particularly to a new and distinctive variety of hybrid tea rose combining grandiflora and floribunda characteristics.

My new and herein disclosed rose plant variety was developed as a result of definite breeding efforts carried on by me since 1954 at Livermore, California, and originated as a seedling derived from a cross of Dean Collins (Plant Pat. 1,279) and Independence (Plant Pat. 1,036), Independence being the pollen parent. I have reproduced this new variety asexually, from buds, at Livermore, California, and continuous reproduction of the new variety through successive asexual propagations, by budding, has proved its novel characteristics to be fixed and to hold true to form.

A primary object of this invention was to produce a commercially superior rose plant having the color of Independencec ombined with the flower size and growth habit of Dean Collins.

This object has been accomplished in my new variety which is particularly distinguished from its parents and all other similar varieties by its relatively large flowers having substantially the coloring of Independence, differing only in minor details, which occur on long cutting stems often up to 3 feet in length; by its abundant and very large leaves which are of greater size than those of either of its parents; and by the distinctive and extraordinary coloring of its sepals which have a red anthocyanin pigment appearing on both surfaces of the sepals.

My new variety of rose plant is shown in full color in the accompanying illustration which shows the blooms in several stages of development as well as the nature of the foliage. The colors shown are substantially true.

The following is a detailed description of the new rose plant variety, the color designations set out being according to the Horticultural Color Chart of The British Colour Council. The specification is for greenhouse grown plants, unless otherwise stated, observed at Livermore, California.

*The plant*

Origin: Seedling.
Parentage:
*Seed parent.*—Dean Collins (Pl. Pat. 1,279).
*Pollen parent.*—Independence (Pl. Pat. 1,036).
Classification: Hybrid of Grandiflora×floribunda. Commercial—very large flowered hybrid tea with floribunda blooming habit.
Form: Medium tall, compact growing bush.
Heighth: 3 to 4 feet in outdoor garden at Livermore, Calif. 6 to 8 feet in one season in hot house.
Growth: Sturdy, vigorous, and upright. Very luxuriant with large canes.
Branching: Very free-branching, but compact in habit.
Strength: Medium.
Foliage:
*Quantity.*—Abundant.

*Number of leaves.*—6 to 8 per flowering stem.
*Size of leaf.*—Very large—4 to 6¼ inches wide x 6 to 8 inches long.
*Shape of leaf.*—Oval.
*Texture.*—Leathery, smooth and glossy, with serrated edges.
*Color.*—Upper side—Spinach Green (0960). Under side—Sage Green (000861) heavily tinged with purple anthocyanin pigment.
*Leaflets.*—Variable in size and number. 5 to 7 per leaf—some leaves near flower have only 3 leaflets.
*Size of leaflets.*—Terminal—1⅝ to 2½ x 2½ to 4 inches. Lateral—1¼ to 2⅛ x 2 to 3 inches.
*Petioles.*—1 inch to 1¾ inches long.
*Ribs and veins.*—Prominent midrib; veins not very noticeable.
*Rachis.*—Unarmed, except for occasional very small spines on underside, often only 1 or 2, rarely 5.
*Thorns.*—Yes. Prickles—no. Size—⅜ inch at base, ¼ inch high and curved strongly downward. Color—yellow, heavily tinged with anthocyanin pigment. No exact matching color in Horticultural Color Chart.

*Bud*

Size: Large.
*Diameter.*—1⅛ to 1¼ inches.
*Depth.*—1½ to 1¾ inches.
Form: Ovoid at first and becoming urn-shaped as bud begins to open. Bud opens slowly to form a high centered imbricated flower which finally becomes cup-shaped with stamens showing.
Color: When sepals first divide—Maroon (1030) at base to Pansy Purple (928). When petals begin to unfurl—Maroon (1030) in ¼ inch arc at base shading to Cardinal Red (822/1).
Sepals: Branched, alternate ones with small ⅛ to 3/16 inch long x 1/16 inch wide lateral appendages. Two sepals have 3 appendages and one sepal has one appendage.
*Form.*—Spear-shaped, and curl back.
*Color.*—Inside—Sage Green (000861/2); center tinged with red anthocyanin pigment. Outside—Lettuce Green (861); edges tinged with red anthocyanin pigment.
Calyx:
*Shape.*—Pear-shaped.
*Size.*—Medium, ½ inch wide, ⅜ inch long. Does not split.
*Aspect.*—Smooth, not hairy or glandular.
Peduncle:
*Length.*—3½ to 4 inches.
*Aspect.*—Smooth, completely free of prickles.
*Strength.*—Strong and erect, 3/16 inch diameter.
*Color.*—Lettuce Green (861) with side toward the sun tinged with purple anthocyanin color.

*Flower*

Blooms: Continuously and profusely, from early spring through late fall.
Size: Very large. 4 to 5 inches in diameter and 2½ to 3 inches in depth.
Borne: Singly. Also in clusters of 2 to 5 blooms.
Shape: High center when gloom first opens, changing later to a cup-shaped fully double flower with the center petals arching over the stamens to partially cover them.
Petalage: 40 to 50 petals, spirally and quite regularly imbricated in arrangement.
*Form.*—Obovate, occasionally notched with a definite apex 1/16 inch high x about ⅛ inch broad at base.

*Color.*—(*a*) In cool environment, 62–75° F.: outer petals—Signal Red (719) shading to Signal Red 719/3 at top, with an arc of Cardinal Red (822/3) at base about ¼ inch deep; inside petals—Signal Red (719/2—719/3); reverse side—Cardinal Red (822/3). (*b*) In warmer environment, 62–98° F.: outer petals—Geranium Lake (20) varying to Orient Red (819); inside petals—Orient Red (819); base and reverse side—substantially the same as (*a*). Petals stay on stem 5 to 6 days.

Petaloids:

*Number.*—9 to 12.

*Size.*—½ to ¾ inch wide x 1 inch long.

*Color.*—Same as petals.

Penduncle:

*Length.*—3½ to 4 inches. Upright and very sturdy—to 3/16 inch diameter.

*Color.*—Scheeles Green (860).

Texture: Intermediate—firm texture but not leathery.

Appearance: Velvety.

Discoloration: Fades to Carmine (21/1) tinged with Carmine (21) and on reverse side to China Rose (024).

Effect of wet or hot weather: In wet cold weather bloom is slower in opening and shows more Carmine color on the upper surface of the petals.

Lasting quality: On plant—4 to 5 days. As a cut flower—3 to 4 days.

Persistence: Best in hot weather. Petals drop clean.

Fragrance: Medium strong hybrid tea fragrance.

Disease resistance: Resistant to mildew and rust, as observed at Livermore, Calif.

*Genital organs*

Stamens:

*Anthers.*—Length—⅛ to 3/16 inch. Arrangement—irregular. Number—many; 125–150 or more on large flower. Color—much anthocyanin color; near Claret Rose (021).

*Filaments.*—Length—⅛ to ¼ inch. Color—Claret Rose (021).

Pollen: Color—Amber Yellow (505).

Pistils:

*Number.*—50 to 75.

*Length.*—¼ to ⅜ inch.

Stigmas: Color—Minosa Yellow (602/1).

Characteristics of ovaries: Normal; cream white with silvery white hairs.

*Fruit*

Fertile, round in shape and yellow in color at maturity.

The distinctive and advantageous characteristics of my new rose variety reside mainly in the fact that it is much superior to its pollen parent Independence, having larger flowers very similar in color occurring on longer cutting stems, often up to three feet long, and having much larger very glossy leaves which provide a very fine "dressed up" effect to the cut flowers, thus making it a commercially excellent variety for cut flower production. Also, because the new variety is a hybrid with the grandiflora Dean Collins, the flowering habit is intermediate and the plant does not require disbudding as much as Independence to produce long cutting stems. Although the new variety does not continue flowering during the short winter days, its prolific production of high quality flowers in spring, summer and fall make up for the lack of winter production.

My new variety resembles Baccara (Pl. Pat. 1,367) in many ways. However, under the same greenhouse growing conditions the following distinctions have been observed:

(*a*) The leaves of the new variety are larger, more glossy, and somewhat less serrate, with the veins showing less prominently than in Baccara.

(*b*) The sepals of the new variety have a slight amount of red anthocyanin pigment on both surfaces, whereas the sepals of Baccara have no red pigment.

(*c*) The color of Baccara is more in the vermilion to scarlet range.

(*d*) The petals of Baccara are more leathery in texture and roll back more as the bloom opens. The flower is therefore stiffer in outline and the bud is not as urn-shaped as in the new variety. Although the petals of the new variety are not as leathery and heavy in texture as Baccara, they are very substantial and absorb enough water when properly stored overnight at 40° F. to last very well as cut flowers. Also, the new variety, though high centered like Baccara at the first phase of bud opening, becomes more cup-shaped when fully open and the inner petals remain upright, tending to cover the stamens and stigmas thus giving a fully double effect; and the petals have enough Cardinal Red undertone from the reverse side to give more of a red rose effect than in the case of Baccara.

(*e*) The new variety is more productive during the main growing season, from March to December, because it has inherited more of the floribunda blooming habit due to its being a cross of an $F_1$ hybrid tea×floribunda crossed back to a floribunda namely Independence. Also, the general habit of Baccara is more "leggy" and thus requires more pruning to be kept in good shape for production.

(*f*) Baccara tends to grow taller than my new variety and has many more thorns, which are very much darker in color; and the new growth of Baccara is much more purple-red, due to a very much greater anthocyanin pigmentation, than is the new growth of the new variety.

Having now described my new variety of rose plant, I claim:

A new and distinct variety of hybrid tea rose plant, substantially as herein shown and described, particularly characterized by its fluoribunda blooming habit and prolific production of very large high quality flowers; by the distinctive red anthocyanin pigmentation appearing on both surfaces of the sepals; by the very large size and abundance of its foliage; by its vigorous, very luxuriant, and free-branching but compact habit of growth; and by its retention of substantially the same red rose color of its pollen parent.

No references cited.